US00RE43583E

(19) United States
(12) Reissued Patent
Arita et al.

(10) Patent Number: US RE43,583 E
(45) Date of Reissued Patent: Aug. 14, 2012

(54) OPHTHALMIC COMPOSITION FOR SOFT CONTACT LENS COMPRISING TERPENOID

(75) Inventors: Harumasa Arita, Osaka (JP); Sakaya Ashikaga, Osaka (JP); Kaori Ogawa, Osaka (JP); Miyuki Nishimura, Osaka (JP)

(73) Assignee: Rohto Pharmaceutical Co., Ltd., Osaka (JP)

(21) Appl. No.: 13/360,032

(22) Filed: Jan. 27, 2012

Related U.S. Patent Documents

Reissue of:
(64) Patent No.: 8,067,038
Issued: Nov. 29, 2011
Appl. No.: 12/304,875
PCT Filed: Jun. 15, 2007
PCT No.: PCT/JP2007/062179
§ 371 (c)(1),
(2), (4) Date: Aug. 12, 2009
PCT Pub. No.: WO2007/145344
PCT Pub. Date: Dec. 21, 2007

(30) Foreign Application Priority Data

Jun. 16, 2006 (JP) ..... 2006-168156

(51) Int. Cl.
*A01N 65/00* (2009.01)

(52) U.S. Cl. ..... 424/725
(58) Field of Classification Search ..... None
See application file for complete search history.

(56) References Cited

U.S. PATENT DOCUMENTS

2006/0073185 A1* 4/2006 Jani et al. ..... 424/427

FOREIGN PATENT DOCUMENTS

| | | |
|---|---|---|
| JP | 2002-332248 | * 11/2002 |
| JP | 3496726 | * 11/2003 |
| JP | 2005-36011 | * 2/2005 |
| WO | WO 99/09968 | * 3/1999 |
| WO | WO 2005/002595 | * 1/2005 |
| WO | WO 2005/025539 | * 3/2005 |

* cited by examiner

*Primary Examiner* — Michael Meller
(74) *Attorney, Agent, or Firm* — Roylance, Abrams, Berdo & Goodman, L.L.P.

(57) ABSTRACT

Disclosed is an ophthalmic composition for a soft contact lens, which is characterized in that the adsorption of a terpenoid contained in the composition onto a soft contact lens is reduced. The ophthalmic composition comprises a combination of Component (A) 0.005 to 0.01 wt % of a terpenoid and Component (B) alginic acid and/or a salt thereof.

4 Claims, No Drawings

OPHTHALMIC COMPOSITION FOR SOFT CONTACT LENS COMPRISING TERPENOID

Matter enclosed in heavy brackets [ ] appears in the original patent but forms no part of this reissue specification; matter printed in italics indicates the additions made by reissue.

TECHNICAL FIELD

The present invention relates to an ophthalmic composition for a soft contact lens (hereinafter referred to as an "SCL"), in which the adsorption of a terpenoid to an SCL is suppressed. The present invention also relates to a method for suppressing the adsorption of a terpenoid to an SCL. Furthermore, the present invention relates to a method for providing, to an ophthalmic composition for an SCL comprising a terpenoid, an effect of suppressing the adsorption of a terpenoid to an SCL.

BACKGROUND ART

Because SCLs are made of materials having a high water content and flexibility, they can provide a more comfortable fit for wearers, and can be worn for a long period of time compared with hard contact lenses. Therefore they have been widely used. With the increase in the number of SCL users, recently, ophthalmic compositions for SCL (including eye drops and eye washes that can be used when wearing SCLs, wetting and rewetting drops for SCL, SCL care solutions, and the like) containing various components have also been proposed. Of these compositions, ophthalmic compositions for SCL comprising a terpenoid such as menthol or camphor have attracted attention, because they are expected to have an effect of alleviating stimulation, thus reducing discomfort, or providing a cool and refreshing feeling.

However, SCLs have a specific problem in that terpenoids adsorb to the SCLs. When terpenoids adsorb to and deposit on an SCL, the SCL may be deformed, and this sometimes causes a decrease in wettability, or an adverse affect on feeling while wearing, such as a foreign-body feeling or discomfort. For this reason, when a terpenoid is added to ophthalmic compositions for SCL (including eye drops and eye washes that can be used when wearing SCLs, wetting and rewetting drops for SCL, SCL care solutions, and the like), it is essential to suppress the adsorption of the terpenoid.

It has hitherto been reported that the addition of a surfactant is effective for reducing the adsorption of a terpenoid to an SCL. When a surfactant is added, however, defects such as coloring of the resulting ophthalmic composition for SCL can be caused depending on the type or proportion of the surfactant; there can also be disadvantages such as difficulty in handling during production because of bubbling. Under such circumstances, the development of a novel technique for suppressing the adsorption of a terpenoid to an SCL has been demanded.

On the other hand, alginic acid forms gel (becoming more viscous) by being partially cross-linked with a divalent or higher valent cation such as a $Ca^{2+}$ ion, and it is already recognized that the alginic acid is an available component in the ophthalmic field (see, for example, Patent Document 1). Furthermore, it has also been found that when an eye drop comprising alginic acid is applied to an eye, $Ca^{2+}$ ions existing on an ocular mucosa are contacted with the alginic acid to make the eye drop gel (become more viscous) on the ocular mucosa, and therefore the alginic acid is useful for improving the retention of the eye drop on the ocular mucosa and maintaining effects produced by active ingredients. However, it has not been reported that 0.005% by weight or more of a terpenoid is used together with alginic acid in an ophthalmic composition for an SCL. Additionally, it is not entirely understood what effect the alginic acid exerts on the adsorption of the terpenoid within such a concentration range to the SCL.

Patent Document 1—Japanese Patent Application Laid-Open Publication No. 2002-332248

DISCLOSURE OF THE INVENTION

Problems to be Solved by the Invention

An object of the present invention is to solve the problems of the prior art as described above. Specifically, the object of the present invention is to provide an ophthalmic composition for an SCL, in which the adsorption of a terpenoid to an SCL is suppressed. The object of the present invention is also to provide a method for providing, to an ophthalmic composition for an SCL containing a terpenoid, an effect of suppressing the adsorption of a terpenoid to an SCL. Furthermore, the object of the present invention is to provide a method for suppressing the adsorption of a terpenoid to an SCL.

Means for Solving the Problems

As a result of intensive studies for solving the problems described above, the present inventors found that by using alginic acid and/or a salt thereof together with a terpenoid, it is possible to suppress the adsorption of the terpenoid to an SCL and exert effectively useful effects brought by the terpenoid. The present invention has been completed based on this finding and by making further improvements.

Specifically, the present invention provides an ophthalmic composition for SCL as follows.

Item 1: An ophthalmic composition for a soft contact lens comprising Component (A) 0.005 to 0.1% by weight of a terpenoid, and Component (B) alginic acid and/or a salt thereof.

Item 2: The ophthalmic composition for a soft contact lens according to Item 1, wherein Component (A) is at least one member selected from the group consisting of menthol, camphor and menthone.

Item 3: The ophthalmic composition for a soft contact lens according to Item 1, which contains 0.005 to 0.5% by weight of Component (B).

Item 4: The ophthalmic composition for a soft contact lens according to Item 1, which contains 5 to 50,000 parts by weight of Component (B) per 100 parts by weight of Component (A).

Item 5: The ophthalmic composition for a soft contact lens according to Item 1, which has more than 1 value, defining the osmotic pressure of a 0.9 w/v % aqueous sodium chloride solution as 1.

Item 6: The ophthalmic composition for a soft contact lens according to Item 1, which is an eye drop.

Item 7: The ophthalmic composition for a soft contact lens according to Item 1, which is an ophthalmic composition used for a silicone hydrogel soft contact lens.

The present invention also provides a use as follows.

Item 8-1: A use of a composition comprising Component (A) 0.005 to 0.1% by weight of a terpenoid and Component (B) alginic acid and/or a salt thereof for the manufacture of an ophthalmic composition for a soft contact lens.

Item 9-1: The use according to Item 8-1, wherein Component (A) is at least one member selected from the group consisting of menthol, camphor and menthone.

Item 10-1: The use according to Item 8-1, wherein the proportion of Component (B) in the ophthalmic composition for a soft contact lens is 0.005 to 0.5% by weight.

Item 11-1: The use according to Item 8-1, wherein the composition contains 5 to 50,000 parts by weight of Component (B) per 100 parts by weight of Component (A).

Item 12-1: The use according to Item 8, wherein the composition has more than 1 value, defining the osmotic pressure of a 0.9 w/v % aqueous sodium chloride solution as 1.

Item 13-1: The use according to Item 8-1, wherein the ophthalmic composition for a soft contact lens is an eye drop.

Item 14-1: The use according to Item 8-1, wherein the ophthalmic composition for a soft contact lens is an ophthalmic composition used for a silicone hydrogel soft contact lens.

Item 8-2: The use of Component (A) a terpenoid and Component (B) alginic acid and/or a salt thereof for the manufacture of an ophthalmic composition for a soft contact lens that contains Component (A) 0.005 to 0.1% by weight of a terpenoid and Component (B) alginic acid and/or a salt thereof.

Item 9-2: The use according to Item 8-2, wherein Component (A) is at least one member selected from the group consisting of menthol, camphor and menthone.

Item 10-2: The use according to Item 8-2, wherein the proportion of Component (B) in the ophthalmic composition for a soft contact lens is 0.005 to 0.5% by weight.

Item 11-2: The use according to Item 8-2, wherein the ophthalmic composition for a soft contact lens contains 5 to 50,000 parts by weight of Component (B) per 100 parts by weight of Component (A).

Item 12-2: The use according to Item 8-2, wherein the ophthalmic composition for a soft contact lens has more than 1 value, defining the osmotic pressure of a 0.9 w/v % aqueous sodium chloride solution as 1.

Item 13-2: The use according to Item 8-2, wherein the ophthalmic composition for a soft contact lens is an eye drop.

Item 14-2: The use according to Item 8-2, wherein the ophthalmic composition for a soft contact lens is an ophthalmic composition used for a silicone hydrogel soft contact lens.

Furthermore, the present invention provides a method for suppressing the adsorption of a terpenoid as follows.

Item 15: A method for suppressing the adsorption of a terpenoid to a soft contact lens, comprising a step of contacting an ophthalmic composition for a soft contact lens that contains Component (A) 0.005 to 0.1% by weight of a terpenoid and Component (B) alginic acid and/or a salt thereof with a soft contact lens.

Item 16: The method according to Item 15, wherein Component (A) is at least one member selected from the group consisting of menthol, camphor and menthone.

Item 17: The method according to Item 15, wherein the proportion of Component (B) in the ophthalmic composition for a soft contact lens is 0.005 to 0.5% by weight.

Item 18: The method according to Item 15, wherein the ophthalmic composition for a soft contact lens contains 5 to 50,000 parts by weight of Component (B) per 100 parts by weight of Component (A).

Item 19: The method according to Item 15, wherein the ophthalmic composition for a soft contact lens has more than 1 value, defining the osmotic pressure of a 0.9 w/v % aqueous sodium chloride solution as 1.

Item 20: The method according to Item 15, wherein the ophthalmic composition for a soft contact lens is an eye drop.

Item 21: The method according to Item 15, wherein the ophthalmic composition for a soft contact lens is an ophthalmic composition used for a silicone hydrogel soft contact lens.

Item 22: The method according to Item 15, which is a method for suppressing the adsorption of a terpenoid to a soft contact lens in applying an eye drop or washing eyes, and which comprises a step of applying the ophthalmic composition for a soft contact lens to an eye wearing a soft contact lens.

Furthermore, the present invention provides a method for providing an effect of suppressing the adsorption of a terpenoid.

Item 23: A method for providing, to an ophthalmic composition for a soft contact lens that contains a terpenoid, an effect of suppressing the adsorption of a terpenoid to a soft contact lens, which comprises a step of mixing Component (B) alginic acid and/or a salt thereof with an ophthalmic composition for a soft contact lens that contains Component (A) 0.005 to 0.1% by weight of a terpenoid.

Item 24: The method according to Item 23, wherein Component (A) is at least one member selected from the group consisting of menthol, camphor and menthone.

Item 25: The method according to Item 23, wherein Component (B) is added to the ophthalmic composition for a soft contact lens in such a manner that the proportion of Component (B) becomes 0.005 to 0.5% by weight.

Item 26: The method according to Item 23, wherein Component (B) is added so that its ratio becomes 5 to 50,000 parts by weight per 100 parts by weight of Component (A) in the ophthalmic composition for a soft contact lens.

Item 27: The method according to Item 23, wherein the ophthalmic composition for a soft contact lens containing Component (B) has more than 1 value, defining the osmotic pressure of a 0.9 w/v % aqueous sodium chloride solution as 1.

Item 28: The method according to Item 23, wherein the ophthalmic composition for a soft contact lens is an eye drop.

Item 29: The method according to Item 23, wherein the ophthalmic composition for a soft contact lens is an ophthalmic composition used for a silicone hydrogel soft contact lens.

Effects of the Invention

In the ophthalmic composition for SCL of the present invention, the adsorption of a terpenoid to an SCL is suppressed, thereby suppressing the distortion of the shape of the SCL, and improving the wettability, reducing foreign-body feeling and discomfort to improve the feeling during wear.

Additionally, the ophthalmic composition for SCL of the present invention has an advantage in that the adsorption of a terpenoid to an SCL can be suppressed without using a surfactant, or by using only a small amount of a surfactant.

Furthermore, alginic acid and/or a salt thereof contained in the ophthalmic composition for SCL of the present invention have a property that if they are applied to an ocular mucosa, they are contacted with $Ca^{2+}$ ions existing on the ocular mucosa to form a gel. Accordingly, in the ophthalmic composition for SCL of the present invention, the effect of gelation allows the terpenoid to remain on the ocular mucosa for a long period of time, thereby more effectively producing the useful effects inherent in the terpenoid (for example, effects of alleviating stimulation to reduce discomfort, or of producing a cool and refreshing feeling).

Still further, by using the method for suppressing the adsorption of a terpenoid of the present invention, the adsorption of a terpenoid to an SCL can be readily suppressed. Therefore, the method of the present invention is useful for effectively exerting the effects brought by a terpenoid when being used for an eye drop or washing eyes in wearing the SCLs, or caring the SCLs.

BEST MODE FOR CARRYING OUT THE INVENTION (I) Ophthalmic Composition for SCL

The ophthalmic composition for SCL of the present invention comprises Component (A) a terpenoid (that may be simply referred to as Component (A) herein).

The terpenoid used in the present invention is not particularly limited so long as it is pharmacologically or physiologically acceptable, and can be used in the ophthalmic field. Specific examples of the terpenoid include menthol, menthone, camphor, borneol, geraniol, cineol, citronellol, carvone, anethole, eugenol, linalyl acetate, and the like. These compounds may be in any form, such a d-form, an l-form or a dl-form. Also, in the present invention, an essential oil containing the compound as described above may be used as the terpenoid. Examples of such an essential oil include, for example, eucalyptus oil, bergamot oil, pepper mint oil, cool mint oil, spearmint oil, mentha oil, fennel oil, cinnamon oil, rose oil, and the like.

Of these terpenoids, menthol, menthone, camphor, borneol, geraniol, and linalyl acetate are preferable, and the examples of the essential oil containing them include bergamot oil, cool mint oil, mentha oil, rose oil and the like. Menthol, camphor, menthone, geraniol and borneol are more preferable, and the examples of the essential oil containing them include cool mint oil, mentha oil, rose oil and the like. Menthol, camphor and menthone are particularly preferable, and the examples of the essential oil containing them include cool mint oil, mentha oil and the like. In the ophthalmic composition for SCL of the present invention, particularly, the effect of suppressing the adsorption of these terpenoids to contact lenses can be particularly effectively exerted. The terpenoids described above can be used alone or in any combination of two or more types thereof.

The proportion of Component (A) as described above may be from 0.005 to 0.1% by weight based on the total weight of the ophthalmic composition for SCL of the present invention. By containing the terpenoid within such a range, the ophthalmic composition for SCL of the present invention can effectively exert the effect of suppressing the adsorption of the terpenoid to the SCL. If the proportion of Component (A) is 0.001% by weight or less, as shown in the Comparative Examples below, it tends to fail to exert the effect of suppressing the adsorption of the terpenoid to the SCL. The range of the total proportion of Component (A) is preferably from 0.01 to 0.08% by weight, more preferably from 0.02 to 0.08% by weight, particularly preferably from 0.025 to 0.075% by weight in the ophthalmic composition for SCL.

The ophthalmic composition for SCL of the present invention comprises Component (B) alginic acid and/or a salt thereof (which may be simply referred to as Component (B) herein), together with the specified proportion of Component (A) as described above. By adding Component (B), it is possible that the adsorption of the specified proportion of Component (A) to an SCL can be effectively suppressed, and useful effects brought by Component (A) can be effectively exerted.

The alginic acid is a polysaccharide composed of mannuronic acid (which may be hereinafter simply referred to as "M") and guluronic acid (which may be hereinafter simply referred to as "G"), which is a block copolymer in which homopolymer fractions of mannuronic acid (MM fractions), homopolymer fractions of guluronic acid (GG fractions) and fractions of the randomly arranged mannuronic acid and guluronic acid (MG fractions) are randomly bonded.

For the alginic acid used in the present invention, the composition ratio of mannuronic acid to guluronic acid (M/G ratio; molar ratio) is not particularly limited. For example, alginic acid with an M/G ratio ranging from 0.4 to 4.0 is widely used. The smaller the M/G ratio, the more gelation of the composition tends to be initiated. It is desirable that the M/G ratio be 2.5 or less, preferably 2.0 or less, more preferably 1.6 or less, from the viewpoint of improvement in the retention of the terpenoid or other pharmacologically active ingredients on application sites. In particular, from the viewpoint of further improvement in the effect that is more effectively suppressing the adsorption of Component (A) to an SCL in the ophthalmic composition for SCL of the present invention, it is desirable to use alginic acid having an M/G ratio ranging preferably from 0.4 to 2.0, more preferably from 0.5 to 1.6, and particularly preferably from 1.0 to 1.6. In the present invention, the M/G ratio is a value calculated by dividing alginic acid into block units, fractionating them, and quantifying each of them; it is specifically determined in accordance with the method described in A. Haug et al., Carbohyd. Res. 32 (1974), p. 217-225.

In the alginic acid used in the present invention, the ratio of the MM fraction, the GG fraction and the MG fraction is not particularly limited, and may be appropriately selected depending on the application or the form of the aqueous composition.

In the present invention, alginic acid with a molecular weight ranging from low to high can be appropriately used.

The salts of the alginic acid are not specifically limited so long as they are pharmacologically or physiologically acceptable. Specifically, examples of the usable salts of the alginic acid include sodium salt, potassium salt, triethanol amine salt, ammonium salt, and the like. The salts of the alginic acid may be used alone or in any combination of two or more types thereof.

In the ophthalmic composition for SCL of the present invention, a single type of alginic acid or a salt thereof may be used, and any two or more types of alginic acid and a salt thereof may be used. In particular, alginic acid, sodium alginate and potassium alginate are water-soluble, and are preferably used in the present invention.

In the ophthalmic composition for SCL of the present invention, from the viewpoint of more-effectively suppressing the adsorption of Component (A) to an SCL, the ratio of Component (B) to Component (A) can be selected as follows. It is desirable that based on 100 parts by weight of the total weight of Component (A), the total weight of Component (B) is from 5 to 50,000 parts by weight, preferably from 10 to 8,000 parts by weight, more preferably from 20 to 5,000 parts by weight, further more preferably from 20 to 2,000 parts by weight, and particularly preferably from 50 to 2,000 parts by weight. By selecting the ratio of Component (B) to Component (A) as described above, it is possible to enhance the suppression in the adsorption of terpenoid to an SCL, and the improvement of sense of use.

Additionally, the proportion of Component (B) in the ophthalmic composition for SCL of the present invention is not particularly limited, and can be appropriately selected depending on the types of Components (A) and (B) used, the ratio of Components (A) to (B), the application or form of the composition and the like. As an example of the proportion of Component (B), the total proportion of Component (B) of from 0.005 to 0.5% by weight, preferably from 0.01 to 0.25% by weight, and more preferably from 0.02 to 0.1% by weight based on the total weight of the ophthalmic composition for SCL are listed.

The ophthalmic composition for SCL of the present invention may further contain a buffer agent. By adding the buffer agent, the adsorption of Component (A) to the SCL may be more effectively suppressed. The buffer agents that can be added to the ophthalmic composition for SCL of the present invention are not particularly limited so long as they are pharmacologically or physiologically acceptable. Examples of the buffer agent include boric acid buffer agents, phosphoric acid buffer agents, carbonic acid buffer agents, citric acid buffer agents, acetic acid buffer agents, epsilon-aminocaproic acid, aspartic acid, salts of aspartic acid, and the like. These buffer agents may be used in combination. Preferable buffer agents include boric acid buffer agents, phosphoric acid buffer agents, carbonic acid buffer agents and citric acid buffer agents. Particularly preferable buffer agents include boric acid buffer agents, citric acid buffer agents and phosphoric acid buffer agents. Examples of the boric acid buffer agent include salts of boric acid, such as alkali metal salts of boric acid and alkaline earth metal salts of boric acid. Examples of the phosphoric acid buffer agent include salts of phosphoric acid such as alkali metal salts of phosphoric acid and alkaline earth metal salts of phosphoric acid. Examples of the citric acid buffer agent include citric acid alkali metal salts, citric acid alkaline earth metal salts, and the like. Hydrates of boric acid salts and phosphoric acid salts may be used as the boric acid buffer agent and the phosphoric acid buffer agent, respectively. More specifically, examples include boric acid or salts thereof (sodium borate, potassium tetraborate, potassium metaborate, ammonium borate, borax, and the like); phosphoric acid or salts thereof (disodium hydrogen phosphate, sodium dihydrogen phosphate, potassium dihydrogen phosphate, trisodium phosphate, dipotassium phosphate, calcium monohydrogen phosphate, calcium dihydrogen phosphate, and the like); carbonic acid or salts thereof (sodium hydrogen carbonate, sodium carbonate, ammonium carbonate, potassium carbonate, calcium carbonate, potassium hydrogen carbonate, magnesium carbonate, and the like); citric acid or salts thereof (sodium citrate, potassium citrate, calcium citrate, sodium dihydrogen citrate, disodium citrate, and the like); acetic acid or salts thereof (ammonium acetate, potassium acetate, calcium acetate, sodium acetate, and the like); aspartic acid or salts thereof (sodium aspartate, magnesium aspartate, potassium aspartate, and the like), and the like. The buffer agent may be used alone or in any combination of two or more types thereof.

When the buffer agent is mixed in the ophthalmic composition for SCL of the present invention, the proportion of the buffer agent depends on the types of the buffer agent used and effects to be expected, and cannot be uniformly defined. For example, the total proportion of the buffer agent may be from 0.001 to 10% by weight, preferably from 0.1 to 5% by weight of the total weight of the ophthalmic composition for SCL. More specifically, when a boric acid buffer agent or a phosphoric acid buffer agent is used, the proportion of the buffer agent in the ophthalmic composition for SCL may be, for example, from 0.0001 to 10% by weight, preferably from 0.01 to 5% by weight; when a carbonic acid buffer agent is used, it may be, for example, from 0.001 to 5% by weight, preferably from 0.005 to 3% by weight; when a citric acid buffer agent is used, it may be, for example, from 0.001 to 5% by weight, preferably from 0.005 to 3% by weight; when an acetic acid buffer agent is used, it may be, for example, from 0.001 to 5% by weight, preferably from 0.005 to 3% by weight; when an epsilon-aminocaproic acid is used, it may be, for example, from 0.005 to 10% by weight, preferably from 0.01 to 5% by weight; and when an aspartic acid or a salt thereof is used, it may be, for example, from 0.005 to 10% by weight, preferably from 0.01 to 5% by weight.

The ophthalmic composition for SCL of the present invention is in the state of liquid or gel, and preferably is in the state of liquid. Ophthalmically acceptable water, preferably purified water or extrapure water is used as a base of the composition.

The pH of the ophthalmic composition for SCL of the present invention is not particularly limited, so long as it is within a pharmacologically or physiologically acceptable range. The pH of the ophthalmic composition for SCL of the present invention may be, for example, in a range of from 5 to 9, preferably from 5.5 to 8.5, and more preferably from 6 to 8. When the pH range of the composition for a contact lens of the present invention is adjusted to the range described above, the effect of suppressing the adsorption of Component (A) to the SCL can be more effectively exerted. Additionally, if the pH is within the above-mentioned range, the composition can be safely applied to eyes or lenses, and ophthalmic preparations therefrom can be practically used.

Further, the ratio of osmotic pressure of the ophthalmic composition for SCL of the present invention may be adjusted to a ratio within a range acceptable for living bodies, if necessary. An appropriate ratio of osmotic pressure depends on the application or the state of the composition, and generally, it may be from 0.2 to 1.8. In order to more effectively suppress the adsorption of a terpenoid to an SCL, however, it is desirable that the ratio of osmotic pressure is more than 1, more preferably from 1.1 to 1.6, particularly preferably from 1.1 to 1.4.

In the ophthalmic composition for SCL of the present invention, the ratio of osmotic pressure is defined as a ratio of osmotic pressure of a sample, calculated when an osmotic pressure of a 0.9 w/v % aqueous sodium chloride solution is regarded as 1, based on the Japanese Pharmacopoeia Fourteenth Edition, and the osmotic pressure is measured in accordance with the method for measuring osmotic pressure (freezing point depression method) described in the Japanese Pharmacopoeia. A standard solution for measuring a ratio of an osmotic pressure is prepared by drying sodium chloride (the Japanese Pharmacopoeia standard reagent) at 500 to 650° C. for 40 to 50 minutes, allowing it to cool in a desiccator (silica gel), precisely weighing out 0.900 grams thereof, dissolving it in purified water, and precisely adjusting the amount of the solution to 100 mL. Alternatively, a commercially available standard solution for measuring a ratio of an osmotic pressure (0.9 w/v % aqueous sodium chloride solution) may be used.

The pH and the ratio of osmotic pressure can be adjusted by a known method in the art using an inorganic salt, a polyhydric alcohol, a sugar alcohol, a saccharide, or the like.

The addition of a surfactant is useful for improving the solubility of the mixed components including a terpenoid. However, depending on the types and concentration of the surfactant, it may cause problems such that the ophthalmic composition for SCL is colored, the surfactant itself may adsorb to an SCL and adversely affect on the wearing comfort, or handling becomes difficult during production because bubbling may increase. In order to avoid the above disadvantages, the ophthalmic composition for SCL of the present invention does not have to contain a surfactant. Even if it contains a surfactant, however, when the total weight of the surfactant is 0.2% by weight or less of the total weight of the ophthalmic composition for SCL, the disadvantages can be avoided and the solubility of the mixed components can be improved. When the surfactant is added, the proportion thereof is preferably from 0.00001 to 0.2% by weight, more preferably from 0.0001 to 0.1% by weight, particularly preferably from 0.001 to 0.05% by weight. Preferable examples of the surfactant include nonionic surfactants. Of these, polyoxyethylene (hereinafter may be referred to as "POE"), sorbitan fatty acid esters (polysorbate 80, polysorbate 65, polysorbate 60, polysorbate 20, and the like), POE hardened castor oils (POE hardened castor oil 5, POE hardened castor oil 10, POE hardened castor oil 20, POE hardened castor oil 40, POE hardened castor oil 50, POE hardened castor oil 60, and POE hardened castor oil 100) are preferable, and polysorbate 80 and POE hardened castor oil 60 are particularly preferable.

Although the addition of a preservative is effective for providing a preservative effect to the ophthalmic composition for SCL, the preservative itself may sometimes adsorb to the SCL, thereby adversely influencing on the wearing comfort. In order to avoid the influence, the ophthalmic composition for SCL of the present invention does not have to contain any preservative. Even if it contains a preservative, when the proportion thereof is 0.1% by weight or less of the total weight of the ophthalmic composition for SCL, the adverse influence can be suppressed while the preservative effect can be achieved. When the preservative is added, the proportion thereof is preferably from 0.00001 to 0.1% by weight, more preferably from 0 to 0.01% by weight, particularly preferably from 0.0001 to 0.001% by weight. Examples of the preservative include quaternary ammonium salts, paraben, sorbic acid, chlorhexidine, and the like. Of these, from the viewpoints described above, preservatives having a weight average molecular weight of 1,500 or more are preferable, and polyhexamethylene biguanide and/or salts thereof are particularly preferable.

So long as the effects of the present invention are not impaired, the ophthalmic composition for SCL of the present invention may contain various components (including pharmacologically active components and physiologically active components) in any combination, in addition to the components as described above. The types of such components are not particularly limited, and for example, active ingredients contained in various medicines described in Nonprescription Drug Manufacturing (Importing) Approval Standard 2000 Edition (under the supervision of Yakuji Shinsa Kenkyukai (Pharmaceutical Examining Society)) can be listed. Specifically, the component used in the ophthalmic drug is as follows.

Epinephrine, epinephrine hydrochloride, ephedrine hydrochloride, tetrahydrozoline hydrochloride, naphazoline hydrochloride, naphazoline nitrate, phenylephrine hydrochloride, methylephedrine hydrochloride, neostigmine methylsulfate, zinc sulfate, zinc lactate, allantoin, epsilon-aminocaproic acid, lysozyme chloride, sodium azulene sulfonate, dipotassium glycyrrhizinate, berberine chloride, berberine sulfate, diphenhydramine hydrochloride, chlorpheniramine maleate, retinol acetate, retinol palmitate, pyridoxine hydrochloride, flavin adenine dinucleotide sodium, cyanocobalamin, panthenol, calcium pantothenate, sodium pantothenate, tocopherol acetate, aminoethylsulfonic acid (taurine), potassium aspartate, magnesium aspartate, a mixture of magnesium aspartate and potassium aspartate, sulfamethoxazole, sulfisoxazole, sulfamethoxazole sodium, sulfisomidine sodium, glucose, sodium hyaluronate, sodium chondroitin sulfate, hydroxyethyl cellulose, hydroxypropylmethyl cellulose, methyl cellulose, polyvinyl alcohol (completely or partially saponified compound), polyvinyl pyrrolidone, and the like are listed.

Further, in order to prepare the ophthalmic composition for SCL of the present invention into a desired form, various components and additives are appropriately selected and one type or any combination thereof may be mixed with the ophthalmic composition for SCL of the present invention according to a conventional method, so long as the effects of the present invention are not impaired. Examples of the component and the additive include, for example, various additives described in Pharmaceutical Excipients Directory 2005 (edited by Japan Pharmaceutical Excipients Council). Typical additives are listed as follows.

Macrogol, poloxamer, poloxamine, alkyl diaminoethylglycine, benzalkonium chloride, polyhexamethylene biguanide hydrochloride, potassium chloride, sodium chloride, calcium chloride, magnesium sulfate, glycerin, propylene glycol, sodium edetate, citric acid, trometamol, and the like are listed.

The form or the application of the ophthalmic composition for SCL of the present invention is not limited, as long as the composition is used so as to bring it into contact with an SCL. For example, eye drops for SCL (eye drops that can be applied to eyes wearing SCLs), eye washes for SCL (eye washes that can be used for eyes wearing SCLs), wetting and rewetting drops for SCL, SCL care solutions (disinfecting solutions for SCLs, storage solutions for SCLs, and washing and storage solutions for SCLs), and the like can be listed. The eye drops and the eye washes for the SCL are preferable, from the viewpoints of easy use and useful effects (effects such a cool sensation, a reduced feeling of the presence of a foreign body, and the like) caused by the terpenoid.

A method for using the ophthalmic composition for SCL of the present invention is not particularly limited, as long as it is a known method comprising a step of contacting the ophthalmic composition for SCL with an SCL. For example, in the case of an eye drop, the eye drop may be applied to the eyes in an appropriate amount before, during or just when wearing SCLs. In the case of an eye wash, the eye wash may also be used in an appropriate amount before, during or just when wearing SCL. In the case of a wetting and rewetting drop for an SCL, the wetting and rewetting drop may be used by contacting an appropriate amount thereof with an SCL on use of the SCL. In the case of a care agent for SCL, the care agent may be used by contacting an appropriate amount thereof with the SCL.

The ophthalmic composition for SCL of the present invention can be used for any types of SCLs. Although the terpenoid tends to easily adsorb to SCLs, particularly to silicone hydrogel SCLs, according to the present invention, an effect of suppressing the adsorption can be effectively exerted to such type of the SCLs. For this reason, in one preferable embodiment of the present invention, a silicone hydrogel SCL is used. Herein, a silicone hydrogel SCL refers to an SCL produced using a silicone hydrogel as at least a part of the starting compound (material).

The ophthalmic composition for SCL of the present invention is prepared according to a known method. For example, Component (A), Component (B) and, if necessary, other components may be added to an aqueous solvent such as purified water or physiological saline to desired concentrations, and performed according to a conventional method.

(II) Method for Suppressing the Adsorption of Terpenoid to SCL

The present invention also provides a method for suppressing the adsorption of a terpenoid to an SCL. The method for suppressing the adsorption of a terpenoid to an SCL comprises a step of contacting the ophthalmic composition for SCL described in Item (I) above (hereunder this composition may be referred to as the ophthalmic composition for SCL (I)) with a soft contact lens.

In the method for suppressing the adsorption of the present invention, contacting of the ophthalmic composition for SCL (I) with an SCL may be performed according to a conventional method depending on the form or the application of the used composition. Specifically, the ophthalmic composition for SCL can be contacted with an SCL by using the ophthalmic composition for SCL according to the method for using the ophthalmic composition for SCL (I).

(III) Method for Providing Effect of Suppressing Adsorption of Terpenoid to SCL

Further, from another viewpoint, the present invention provides a method for providing, to an ophthalmic composition for a soft contact lens that contains a terpenoid, an effect of suppressing the adsorption of the terpenoid to a soft contact lens. The method for providing the effect of reducing the adsorption to the SCL of the present invention comprises a step of mixing Component (B) alginic acid and/or a salt thereof with an ophthalmic composition for a soft contact lens that contains 0.005 to 0.1% by weight of a terpenoid.

In the methods of the present invention, the types and the proportions of Components (A) and (B), other mixed components are as described in the Item (I) Ophthalmic Composition for SCL (I).

EXAMPLES

The following test examples and examples illustrate the present invention in more detail, but are not to be construed to limit the scope thereof.

Test Example 1

The following tests were conducted to examine the effect of alginic acid and/or a salt thereof on the adsorption of a terpenoid to an SCL.

Material for Test

The ophthalmic compositions for SCL shown in Table 1 below (Example 1 and Comparative Example 1) were prepared according to a conventional method. In this test, an SCL (trade name "$O_2$ OPTIX", produced by Ciba Vision Corporation; hydrous; main material: silicone hydrogel; soft contact lens classification: Group I) was used.

Test Method

Each SCL was soaked in 5 mL of saline defined in the Japanese Pharmacopoeia, and was allowed to stand at room temperature (about 25° C.) for about 24 hours. Then, the SCL was removed from the saline, and the moisture was wiped off gently. To a highly hermetic and transparent glass vial, each 20 mL of ophthalmic compositions for SCL of Example 1 and Comparative Example 1 was added. The obtained SCL was soaked in each of the ophthalmic compositions for SCL, which was shaken at a frequency of 120 times/minute at 34° C. for about 24 hours, and the SCL was taken out. Then, the concentration of the terpenoid remaining in each ophthalmic composition for SCL after soaking the SCL (hereinafter referred to as a concentration of TRP after the test) was measured using gas chromatography. A blank test was carried out in the same manner as above, except that an SCL was not soaked, and a concentration of the terpenoid remaining in each of the ophthalmic composition for SCL in the case where the SCL was not soaked (hereinafter referred to as a blank concentration of TRP) was measured.

Based on the measured concentrations of the terpenoid, the amount of the adsorption of the terpenoid (μg/SCL) was calculated and the percentage of prevented adsorption of the terpenoid (%) was obtained in accordance with the following equations.

Amount of adsorption of terpenoid (μg/SCl)={blank concentration of TRP (μg/mL)−concentration of TRP after test (μg/mL)}×20 mL Percentage of suppressed adsorption of terpenoid (%)={1−(amount of adsorption of terpenoid in Example/amount of adsorption of terpenoid in Comparative Example corresponding to the Example)}×100 Equation 1

The results are collectively shown in Table 1. In the ophthalmic composition for SCL of Comparative Example 1, large amounts of menthol, camphor and cool mint oil (containing menthone) adsorbed on the SCL. On the other hand, in the ophthalmic composition for SCL of Example 1 in which alginic acid was added, the amounts of adsorption of menthol, camphor and cool mint oil (containing menthone) to the SCL were remarkably reduced. These results revealed that alginic acid has the effect of reducing the adsorption of a terpenoid to an SCL.

TABLE 1

| Mixed component (% by weight) | | Example 1 | Comparative Example 1 |
|---|---|---|---|
| Terpenoid | 1-Menthol | 0.012 | 0.012 |
| | d-camphor | 0.01 | 0.01 |
| | Cool mint oil* | 0.005 | 0.005 |
| Alginic acid | | 0.05 | — |
| Sodium chloride | | 0.44 | 0.44 |
| Potassium chloride | | 0.08 | 0.08 |
| Boric acid | | 1.0 | 1.0 |
| Borax | | 0.2 | 0.2 |
| Hydroxypropylmethyl cellulose | | 0.15 | 0.15 |
| EDTA | | 0.03 | 0.03 |
| Polyoxyethylene hardened castor oil | | 0.05 | 0.05 |
| Poloxamer 407 | | 0.05 | 0.05 |
| Hydrochloric acid | | Appropriate amount | Appropriate amount |
| Sodium hydroxide | | Appropriate amount | Appropriate amount |
| Purified water | | Appropriate amount | Appropriate amount |
| Total amount | | 100 mL | 100 mL |
| Ratio of osmotic pressure# | | 1.2 | 1.2 |
| pH | | 7.2 | 7.2 |
| Percentage of suppressed adsorption of 1-menthol (%) | | 20.1 | — |
| Percentage of suppressed adsorption of d-camphor (%) | | 29.7 | — |
| Percentage of suppressed adsorption of menthone (%) | | 23.2 | — |

*Cool mint oil is a mixture of pepper mint oil and menthol.

#The ratio of osmotic pressure is represented as the calculated value defining an osmotic pressure of a 0.9 w/v % aqueous sodium chloride solution as 1.

Test Example 2

Ophthalmic compositions for SCL shown in Table 2 below (Example 2 and Comparative Example 2) were prepared, and the effect of suppressing the adsorption of a terpenoid to an SCL was evaluated. Specifically, ophthalmic compositions for SCL shown in Table 2 below (Example 2 and Comparative Example 2), and an SCL (trade name "DuraSoft Colors Tint Green"; produced by Ciba Vision Corporation hydrous, main material: phemfilcon A, soft contact lens classification: Group III) were used to evaluate the effect of suppressing the adsorption of a terpenoid to an SCL using the same manner as that in Test Example 1 as described above.

The results are collectively shown in Table 2. Similarly to the results in Test Example 1 as described above, in the ophthalmic composition for SCL of Example 2 in which alginic acid was mixed, the amounts of the adsorption of menthol, camphor and cool mint oil (containing menthone) were remarkably reduced.

TABLE 2

| Mixed component (% by weight) | | Example 2 | Comparative Example 2 |
|---|---|---|---|
| Terpenoid | 1-menthol | 0.03 | 0.03 |
| | d-camphor | 0.03 | 0.03 |
| | Cool mint oil* | 0.015 | 0.015 |
| Alginic acid | | 0.05 | — |
| Sodium chloride | | 0.44 | 0.44 |
| Potassium chloride | | 0.08 | 0.08 |
| Boric acid | | 1.0 | 1.0 |
| Borax | | 0.2 | 0.2 |
| Polysorbate 80 | | 0.01 | 0.01 |
| Hydrochloric acid | | Appropriate amount | Appropriate amount |
| Sodium hydroxide | | Appropriate amount | Appropriate amount |
| Purified water | | Appropriate amount | Appropriate amount |
| Total volume | | 100 mL | 100 mL |
| Ratio of osmotic pressure# | | 1.2 | 1.2 |
| pH | | 7.2 | 7.2 |
| Percentage of suppressed adsorption of 1-menthol (%) | | 35.7 | — |
| Percentage of suppressed adsorption of d-camphor (%) | | 38.2 | — |
| Percentage of suppressed adsorption of menthone (%) | | 37.9 | — |

*Cool mint oil is a mixture of pepper mint oil and menthol.

#The ratio of osmotic pressure is represented as the calculated value defining an osmotic pressure of a 0.9 w/v % aqueous sodium chloride solution as 1.

Test Example 3

The ophthalmic compositions for SCL shown in Table 3 below (Example 3 and Comparative Example 3) were prepared, and the effect of suppressing the adsorption of a terpenoid to an SCL was evaluated. Specifically, the ophthalmic compositions for SCL shown in Table 3 below (Example 3 and Comparative Example 3), and SCLs (trade name "$O_2$ OPTIX", produced by Ciba Vision Corporation; hydrous; main material: silicone hydrogel; soft contact lens classification: Group I) were used to evaluate the effect of suppressing the adsorption of a terpenoid to an SCL in the same manner as that in Test Example 1 as described above.

As a result, it was confirmed that in the ophthalmic composition for SCL of Example 3 in which alginic acid was mixed, the amounts of the adsorption of borneol and geraniol to the SCL were reduced.

TABLE 3

| Mixed component (% by weight) | | Example 3 | Comparative Example 3 |
|---|---|---|---|
| Terpenoid | d-borneol | 0.005 | 0.005 |
| | geraniol | 0.005 | 0.005 |
| Alginic acid | | 0.05 | — |
| Sodium chloride | | 0.44 | 0.44 |
| Potassium chloride | | 0.08 | 0.08 |
| Boric acid | | 1.0 | 1.0 |
| Borax | | 0.2 | 0.2 |
| Polysorbate 80 | | 0.01 | 0.01 |
| Hydrochloric acid | | Appropriate amount | Appropriate amount |
| Sodium hydroxide | | Appropriate amount | Appropriate amount |
| Purified water | | Appropriate amount | Appropriate amount |
| Total volume | | 100 mL | 100 mL |
| Ratio of osmotic pressure# | | 1.2 | 1.2 |
| pH | | 7.2 | 7.2 |

#The ratio of osmotic pressure is represented as the calculated value defining an osmotic pressure of a 0.9 w/v % aqueous sodium chloride solution as 1.

Test Example 4

The ophthalmic compositions for SCL shown in Table 4 below (Examples 4 to 8 and Comparative Examples 4 to 8) were prepared, and the effect of suppressing the adsorption of a terpenoid to an SCL was evaluated. Specifically, ophthalmic compositions for SCL shown in Table 4 below (Examples 4 to 8 and Comparative Examples 4 to 8), and SCLs (trade name "$O_2$ OPTIX", produced by Ciba Vision Corporation; hydrous; main material: silicone hydrogel; soft contact lens classification: Group I) were used to evaluate the effects of suppressing the adsorption of a terpenoid to an SCL in the same manner as that in Test Example 1 as described above.

As a result, similarly to Test Examples 1 and 2 as described above, it was confirmed that in the ophthalmic compositions for SCL of Examples 4 to 8, the adsorption of menthol and camphor to the SCL is remarkably suppressed. These results revealed that by containing 50 to 2000 parts by weight of alginic acid per 100 parts by weight of the total weight of the terpenoid, it is possible to obtain a better effect of suppressing the adsorption of a terpenoid to an SCL.

TABLE 4

| Mixed component (weight %) | | Ex. 4 | Comp. Ex. 4 | Ex. 5 | Comp. Ex. 5 | Ex. 6 | Comp. Ex. 6 | Ex. 7 | Comp. Ex. 7 | Ex. 8 | Comp. Ex. 8 |
|---|---|---|---|---|---|---|---|---|---|---|---|
| Terpenoid | 1-menthol | 0.008 | 0.008 | 0.008 | 0.008 | 0.008 | 0.008 | 0.008 | 0.008 | 0.016 | 0.016 |
| | d-camphor | 0.001 | 0.004 | 0.004 | 0.004 | 0.004 | 0.004 | 0.004 | 0.004 | 0.008 | 0.008 |
| Alginic acid | | 0.012 | — | 0.1 | — | 0.24 | — | 0.024 | — | 0.012 | — |
| Sodium chloride | | 0.44 | 0.44 | 0.44 | 0.44 | 0.44 | 0.44 | 0.44 | 0.44 | 0.44 | 0.44 |
| Potassium chloride | | 0.08 | 0.08 | 0.08 | 0.08 | 0.08 | 0.08 | 0.08 | 0.08 | 0.08 | 0.08 |
| Boric acid | | 1.0 | 1.0 | 1.000 | 1.000 | 1.000 | 1.000 | 1.000 | 1.000 | 1.000 | 1.000 |
| Borax | | 0.2 | 0.2 | 0.2 | 0.2 | 0.2 | 0.2 | 0.2 | 0.2 | 0.2 | 0.2 |
| Hydroxypropyl methylcellulose | | 0.15 | 0.15 | 0.15 | 0.15 | 0.15 | 0.15 | 0.15 | 0.15 | 0.15 | 0.15 |
| EDTA | | 0.03 | 0.03 | 0.03 | 0.03 | 0.03 | 0.03 | 0.03 | 0.03 | 0.03 | 0.03 |
| Polysorbate 80 | | 0.02 | 0.02 | 0.02 | 0.02 | 0.02 | 0.02 | 0.02 | 0.02 | 0.2 | 0.2 |
| Hydrochloric acid | | q.s. | q.s. | q.s. | q.s. | q.s. | q.s. | q.s. | q.s. | q.s. | Q.s. |

TABLE 4-continued

| Mixed component (weight %) | Ex. 4 | Comp. Ex. 4 | Ex. 5 | Comp. Ex. 5 | Ex. 6 | Comp. Ex. 6 | Ex. 7 | Comp. Ex. 7 | Ex. 8 | Comp. Ex. 8 |
|---|---|---|---|---|---|---|---|---|---|---|
| Sodium hydroxide | q.s. | q.s. | q.s. | q.s. | q.s. | q.s. | q.s. | q.s. | q.s. | Q.s. |
| Purified water | q.s. | q.s. | q.s. | q.s. | q.s. | q.s. | q.s. | q.s. | q.s. | q.s. |
| Total volume | 100 mL | 100 mL | 100 mL | 100 mL | 100 mL | 100 mL | 100 mL | 100 mL | 100 mL | 100 mL |
| Ratio of osmotic pressure# | 1.2 | 1.2 | 1.2 | 1.2 | 1.2 | 1.2 | 1.2 | 1.2 | 1.2 | 1.2 |
| pH | 7.2 | 7.2 | 7.2 | 7.2 | 7.2 | 7.2 | 7.2 | 7.2 | 7.2 | 7.2 |

#The ratio of osmotic pressure is represented as the calculated value defining an osmotic pressure of a 0.9 w/v % aqueous sodium chloride solution as 1.

Test Example 5

The ophthalmic compositions for SCL shown in Table 5 below (Examples 9 to 11, Comparative Examples 9 to 11 and Comparative Examples A and B) were prepared, and the effect of suppressing the adsorption of a terpenoid to an SCL was evaluated. Specifically, the ophthalmic compositions for SCL shown in Table below (Examples 9 to 11, Comparative Examples 9 to 11, and Comparative Examples A and B), and SCLs (trade name "$O_2$ OPTIX", produced by Ciba Vision Corporation; hydrous; main material: silicone hydrogel; soft contact lens classification: Group I) were used to evaluate the effect of suppressing the adsorption of a terpenoid to an SCL in the same manner as that in Test Example 1 as described above. A percentage of the suppressed adsorption of L-menthol in Comparative Example A was calculated according to the following equation.

$$\text{Percentage of suppressed adsorption of terpenoid (\%)} = \{1-(\text{amount of adsorption of terpenoid in Comparative Example A}/\text{amount of adsorption of terpenoid in Comparative Example B})\}\times 100 \quad \text{Equation 2}$$

The results are shown in Table 5. From these results, it was confirmed that when the proportion of L-menthol in the ophthalmic composition for SCL was 0.001% by weight, the effect of suppressing the adsorption of L-menthol to the SCL was not obtained. On the other hand, it was confirmed that only when the proportion of L-menthol in the ophthalmic composition for SCL was 0.005% by weight or more, the effect of suppressing the adsorption of L-menthol to the SCL was obtained. These results revealed that in order to suppress the adsorption of a terpenoid to an SCL, it is necessary to set the concentration of a terpenoid in an ophthalmic composition for SCL to 0.005% by weight or more.

Test Example 6

The ophthalmic compositions for SCL shown in Table 6 below [storage solutions for SCL (Example 12 and Comparative Example 12) and eye drops (Example 13 and Comparative Example 13)] were prepared. The effects of the ophthalmic compositions for SCL on feeling in wearing an SCL (foreign-body feeling, and discomfort) were examined by conducting the experiment as described below.

For eight test subjects wearing SCLs, each SCL was soaked in 2 mL of storage solutions for SCL of Example 12 and Comparative Example 12 shown in Table 7 below for 24 hours. Then, the SCL taken out from the storage solution for SCL of Example 12 or Comparative Example 12 was put in each of the subjects' right and left eyes. Furthermore, the eye drop of Example 13 shown in Table 7 was applied to the eye on which the SCL treated with the storage solution for SCL of Example 12 was put. Also, similarly to the above, the eye drop of Comparative Example 13 shown in Table 7 was applied to the eye on which the SCL treated with the storage solution for SCL of Comparative Example 12 was put. As the SCL, trade name "$O_2$ OPTIX", produced by Ciba Vision Corporation; hydrous; main material: silicone hydrogel; soft contact lens classification: Group I was used for four of all of the test subjects, and "DuraSoft Colors Tint Green" (produced by Ciba Vision Corporation; hydrous; main material: phemfilcon A; soft contact lens classification: Group III) was used for other four test subjects.

After awhile, a feeling of the presence of a foreign-body and discomfort were evaluated by the test subjects using the ophthalmic compositions for SCL and the results were scored in accordance with the evaluation criteria shown in Table 6 below.

TABLE 5

| Mixed component (% by weight) | Ex. A | Comp. Ex. B | Ex. 9 | Comp. Ex. 9 | Ex. 10 | Comp. Ex. 10 | Ex. 11 | Comp. Ex. 11 |
|---|---|---|---|---|---|---|---|---|
| Terpenoid 1-menthol | 0.001 | 0.001 | 0.005 | 0.005 | 0.01 | 0.01 | 0.01 | 0.01 |
| Alginic acid | 0.1 | — | 0.1 | — | 0.1 | — | 0.1 | — |
| Sodium chloride | 0.4 | 0.4 | 0.7 | 0.7 | 0.7 | 0.7 | 0.4 | 0.4 |
| Potassium chloride | 0.05 | 0.05 | 0.05 | 0.05 | 0.05 | 0.05 | 0.05 | 0.05 |
| Boric acid | 0.5 | 0.5 | 0.5 | 0.5 | 0.5 | 0.5 | 0.5 | 0.5 |
| Borax | 0.55 | 0.55 | 0.55 | 0.55 | 0.55 | 0.55 | 0.55 | 0.55 |
| EDTA | 0.01 | 0.01 | 0.01 | 0.01 | 0.01 | 0.01 | 0.01 | 0.01 |
| Polysorbate 80 | 0.05 | 0.05 | 0.05 | 0.05 | 0.05 | 0.05 | 0.05 | 0.05 |
| Total volume | 100 mL | 100 mL | 100 mL | 100 mL | 100 mL | 100 mL | 100 mL | 100 mL |
| Ratio of osmotic pressure# | 0.9 | 0.9 | 1.3 | 1.3 | 1.3 | 1.3 | 0.9 | 0.9 |
| pH | 7.7 | 7.9 | 7.7 | 7.9 | 7.7 | 7.9 | 7.7 | 7.9 |
| Percentage of suppressed adsorption of 1-menthol (%) | 0 | — | 5.2 | — | 8.5 | — | 7.0 | — |

#The ratio of osmotic pressure is represented as the calculated value defining an osmotic pressure of a 0.9 w/v % aqueous sodium chloride solution as 1.

TABLE 6

| Judged score | Criteria for judgement: Foreign-body | Criteria for judgement: Discomfort |
|---|---|---|
| 3 points | Feel no foreign-body | Feel no discomfort |
| 2 points | Feel little foreign-body | Feel little discomfort |
| 1 point | Feel foreign-body | Feel discomfort |

The results are collectively shown in Table 7. The results revealed that the feeling of the presence of a foreign-body and discomfort were further apparently reduced and better wearing comfort of an SCL could be obtained in the case of using the storage solution for SCL of Example 12 and the eye drop of Example 13, compared to the case using those of Comparative Examples 12 and 13.

TABLE 7

| Mixed component (% by weight) | Example 12 Storage solution for an SCL | Example 13 Eye drop | Comp. Ex. 12 Storage solution for an SCL | Comp. Ex. 13 Eye drop |
|---|---|---|---|---|
| Alginic acid | 0.05 | 0.05 | — | — |
| 1-menthol | 0.005 | 0.005 | 0.005 | 0.005 |
| Sodium chloride | 0.6 | 0.6 | 0.6 | 0.6 |
| Boric acid | 0.8 | 0.8 | 0.8 | 0.8 |

TABLE 7-continued

| Mixed component (% by weight) | Example 12 Storage solution for an SCL | Example 13 Eye drop | Comp. Ex. 12 Storage solution for an SCL | Comp. Ex. 13 Eye drop |
|---|---|---|---|---|
| Borax | 0.15 | 0.15 | 0.15 | 0.15 |
| Hydrochloric acid | q.s. | q.s. | q.s. | q.s. |
| Sodium hydroxide | q.s. | q.s. | q.s. | q.s. |
| Purified water | q.s. | q.s. | q.s. | q.s. |
| Total volume | 100 mL | 100 mL | 100 mL | 100 mL |
| Ratio of osmotic pressure# | 1.2 | 1.2 | 1.2 | 1.2 |
| pH | 7.2 | 7.2 | 7.2 | 7.2 |
| Average of judged score: Foreign-body | 3 points | | 1 point | |
| Average of judged score: Discomfort | 3 points | | 1 point | |

#The ratio of osmotic pressure is represented as the calculated value defining an osmotic pressure of a 0.9 w/v % aqueous sodium chloride solution as 1.

Examples 14 to 33

According to the formulations in Tables 8 to 10 below, eye drops for SCL (Examples 14 to 21 and 26 to 33), a disinfecting solution for SCL (Example 22), a wetting and rewetting solution (Example 23), and eye washes (Examples 24 and 25) were prepared.

TABLE 8

| Mixed component (% by weight) | Example 14 | 15 | 16 | 17 | 18 | 19 | 20 | 21 | 22 | 23 |
|---|---|---|---|---|---|---|---|---|---|---|
| Alginic acid | 0.05 | 0.05 | 0.05 | 0.1 | 0.01 | 0.05 | 0.05 | 0.05 | 0.01 | 0.05 |
| Sodium chloride | q.s. | q.s. | q.s. | q.s. | q.s. | q.s. | q.s. | q.s. | q.s. | q.s. |
| Potassium chloride | 0.08 | 0.08 | 0.08 | 0.08 | 0.08 | 0.08 | 0.08 | 0.08 | 0.08 | 0.08 |
| Boric acid | 1.0 | 1.0 | 1.0 | 1.0 | 1.0 | 1.0 | 1.2 | 1.1 | — | — |
| Borax | 0.2 | 0.2 | 0.2 | 0.2 | 0.2 | 0.2 | 0.25 | 0.25 | — | — |
| Sodium hydrogenphosphate | — | — | — | — | — | — | — | — | 0.2 | 0.2 |
| Sodium dihydrogenphosphate | — | — | — | — | — | — | — | — | 0.015 | 0.04 |
| Sodium edetate | 0.05 | 0.05 | 0.05 | 0.05 | 0.05 | 0.05 | 0.1 | 0.1 | 0.005 | 0.1 |
| Sodium chondroitin sulfate | — | — | — | — | 0.1 | 0.5 | 0.5 | — | — | — |
| Sodium hyaluronate | — | — | — | — | — | — | — | 0.005 | 0.01 | 0.005 |
| Polyvinyl alcohol (GOHSENOL EG-05) | — | — | — | — | — | — | — | — | — | 1.0 |
| Hydroxypropyl methylcellulose (METOLOSE 65SH-4000) | 0.2 | 0.08 | — | — | — | — | — | 0.5 | 0.05 | 0.1 |
| Hydroxyethyl cellulose (Fuji Chemi HEC CF-V) | — | — | 0.07 | 0.07 | — | 0.02 | 0.6 | — | — | — |
| Polyoxyethylene hydrogenated castor oil 60 | 0.05 | 0.05 | 0.05 | — | — | 0.05 | — | 0.05 | — | — |
| Poloxamer 407 | 0.05 | 0.05 | 0.05 | 0.05 | 0.05 | 0.05 | 0.05 | 0.05 | 0.1 | 0.05 |
| Polysorbate 80 | — | — | — | 0.05 | 0.05 | — | 0.05 | — | 0.05 | 0.05 |
| 1-menthol | 0.012 | 0.004 | 0.015 | 0.015 | 0.01 | 0.003 | 0.005 | 0.005 | 0.001 | 0.002 |
| d-camphor | 0.01 | — | 0.01 | 0.01 | 0.005 | — | — | — | — | — |
| Cool mint oil | 0.005 | 0.004 | — | — | — | — | — | — | — | — |
| Geraniol | — | — | — | — | — | 0.003 | — | — | — | 0.001 |
| Borneol | — | — | — | — | 0.003 | — | — | — | — | — |
| Bergamot oil | — | — | — | — | — | — | — | 0.002 | — | 0.001 |
| Polyhexanide hydrochloride | — | — | — | — | — | — | — | — | 0.0001 | 0.00008 |
| Hydrochloric acid | q.s. | q.s. | q.s. | q.s. | q.s. | q.s. | q.s. | q.s. | q.s. | q.s. |

TABLE 8-continued

| Mixed component | Example | | | | | | | | | |
|---|---|---|---|---|---|---|---|---|---|---|
| (% by weight) | 14 | 15 | 16 | 17 | 18 | 19 | 20 | 21 | 22 | 23 |
| Sodium hydroxide | q.s. | q.s. | q.s. | q.s. | q.s. | q.s. | q.s. | q.s. | q.s. | q.s. |
| Purified water | q.s. | q.s. | q.s. | q.s. | q.s. | q.s. | q.s. | q.s. | q.s. | q.s. |
| Total volume | 100 mL | 100 mL | 100 mL | 100 mL | 100 mL | 100 mL | 100 mL | 100 mL | 100 mL | 100 mL |
| pH | 7.2 | 7.2 | 7.4 | 6.5 | 7.0 | 7.5 | 7.3 | 7.5 | 7.8 | 6.0 |
| Ratio of osmotic pressure# | 1.2 | 1.1 | 1.1 | 0.9 | 1.1 | 1.1 | 1.2 | 1.3 | 1.0 | 0.7 |

#The ratio of osmotic pressure is represented as the calculated value defining an osmotic pressure of a 0.9 w/v % aqueous sodium chloride solution as 1.

TABLE 9

| Mixed component | Example | |
|---|---|---|
| (% by weight) | 24 | 25 |
| Alginic acid | 0.05 | 0.05 |
| Sodium chloride | Appropriate amount | Appropriate amount |
| Potassium chloride | 0.08 | 0.08 |
| Boric acid | 1.3 | 1.5 |
| Borax | 0.2 | 0.22 |
| Sodium hydrogen phosphate | — | — |
| sodium dihydrogen phosphate | — | — |
| Sodium edetate | 0.05 | 0.01 |
| Sodium chondroitin sulfate | 0.05 | — |
| Hydroxypropyl methylcellulose (METOLOSE 65SH-4000) | 0.2 | 0.08 |
| Polyoxyethylene hydrogenated castor oil 60 | 0.05 | — |

TABLE 9-continued

| Mixed component | Example | |
|---|---|---|
| (% by weight) | 24 | 25 |
| Poloxamer 407 | 0.05 | 0.05 |
| Polysorbate 80 | — | 0.05 |
| 1-menthol | 0.005 | 0.01 |
| d-camphor | — | 0.003 |
| Hydrochloric acid | Appropriate amount | Appropriate amount |
| Sodium hydroxide | Appropriate amount | Appropriate amount |
| Purified water | Appropriate amount | Appropriate amount |
| Total volume | 100 mL | 100 mL |
| pH | 7.2 | 7.2 |
| Ratio of osmotic pressure# | 1.1 | 1.1 |

#The ratio of osmotic pressure is represented as the calculated value defining an osmotic pressure of a 0.9 w/v % aqueous sodium chloride solution as 1.

TABLE 10

| | Example | | | | | | | |
|---|---|---|---|---|---|---|---|---|
| Mixed component (% by weight) | 26 | 27 | 28 | 29 | 30 | 31 | 32 | 33 |
| Alginic acid | 0.02 | 0.03 | 0.06 | 0.08 | 0.01 | 0.10 | 0.15 | 0.20 |
| Sodium chloride | q.s. | q.s. | q.s. | q.s. | q.s. | q.s. | q.s. | q.s. |
| Potassium chloride | 0.08 | 0.08 | 0.08 | 0.08 | 0.08 | 0.08 | 0.08 | 0.08 |
| Boric acid | 1.00 | — | — | — | — | — | 1.2 | 1.1 |
| Borax | 0.20 | — | — | — | — | — | 0.25 | 0.25 |
| Sodium hydrogen phosphate | — | 0.5 | 1.2 | 1.0 | 0.7 | 0.8 | — | — |
| sodium dihydrogen phosphate | — | — | 0.3 | 0.2 | 0.1 | 0.15 | — | — |
| Sodium edetate | 0.05 | 0.05 | 0.05 | 0.05 | 0.005 | 0.05 | 0.1 | 0.1 |
| Sodium chondroitin sulfate | — | — | — | — | 0.1 | 0.5 | 0.5 | — |
| Sodium hyaluronate | — | — | — | — | — | — | — | 0.005 |
| Metolose 65SH-4000 | 0.2 | 0.0800 | — | — | — | — | — | 0.5 |
| Fuji Chemi HEC CF-V | — | — | 0.07 | 0.07 | — | 0.02 | 0.6 | — |
| Polyoxyethylene hydrogenated castor oil 60 | 0.05 | — | 0.02 | — | 0.05 | 0.01 | — | 0.1 |
| Poloxamer 407 | 0.05 | — | — | — | — | — | — | — |
| Polysorbate 80 | — | 0.08 | — | 0.1 | 0.1 | — | 0.03 | — |
| 1-menthol | 0.012 | 0.02 | 0.015 | 0.005 | 0.01 | 0.008 | 0.01 | 0.015 |
| d-camphor | 0.018 | — | 0.01 | 0.015 | 0.01 | — | — | — |
| Geraniol | — | — | — | — | — | 0.003 | — | — |
| Borneol | — | — | — | — | 0.005 | — | — | — |
| Bergamot oil | — | — | — | — | — | — | — | 0.002 |
| Polyhexanide hydrochloride | — | — | — | — | — | — | 0.00008 | 0.0001 |
| Hydrochloric acid | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. |
| pH | 7.2 | 7.2 | 7.4 | 6.5 | 7.0 | 7.5 | 7.3 | 7.5 |
| Ratio of osmotic pressure# | 1.2 | 1.1 | 1.1 | 1.2 | 1.1 | 1.1 | 1.2 | 1.3 |

#The ratio of osmotic pressure is represented as the calculated value defining an osmotic pressure of a 0.9 w/v % aqueous sodium chloride solution as 1.

The invention claimed is:

1. A method for suppressing adsorption of a terpenoid to a soft contact lens comprising contacting the soft contact lens with an ophthalmic composition comprising 0.005 to 0.1% by weight of a terpenoid and 0.005 to 0.5% by weight of alginic acid and/or a salt thereof whereby the adsorption of the terpenoid to the contact lens is suppressed and wherein the terpenoid is *at least one member* selected from the group consisting of menthol, camphor and menthone.

2. The method according to claim 1, wherein the ophthalmic composition has an osmotic pressure of greater than 1, where the osmotic pressure of a 0.9 w/v % aqueous sodium chloride solution is defined as 1.

3. The method according to claim 1, wherein the ophthalmic composition is an eye drop, and wherein the soft contact lens is worn on the eye when contacted by the ophthalmic composition.

4. The method according to claim 1, wherein the soft contact lens is a silicone hydrogel soft contact lens.

* * * * *

UNITED STATES PATENT AND TRADEMARK OFFICE

CERTIFICATE OF CORRECTION

PATENT NO. : RE43,583 E
APPLICATION NO. : 13/360032
DATED : August 14, 2012
INVENTOR(S) : Harumasa Arita et al.

It is certified that error appears in the above-identified patent and that said Letters Patent is hereby corrected as shown below:

On the Title page of the patent, left column, under INID Code (75), the second-named inventor "Sakaya Ashikaga" should be --Sayaka Ashikaga--

Signed and Sealed this
Sixth Day of November, 2012

David J. Kappos

David J. Kappos
*Director of the United States Patent and Trademark Office*